US006955658B2

(12) United States Patent
Murray, III

(10) Patent No.: US 6,955,658 B2
(45) Date of Patent: Oct. 18, 2005

(54) MOLD FOR FORMING A MEDICAL BALLOON

(75) Inventor: Robert J. Murray, III, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 198 days.

(21) Appl. No.: 10/349,083

(22) Filed: Jan. 23, 2003

(65) Prior Publication Data

US 2004/0147952 A1 Jul. 29, 2004

(51) Int. Cl.$^7$ ......................... A61M 29/00; B29C 49/48
(52) U.S. Cl. ................. 604/103.07; 425/470; 425/522; 606/194; 623/1.11
(58) Field of Search ............................... 425/522, 403, 425/470; 264/573; 604/103.07; 606/194; 623/1.11

(56) References Cited

U.S. PATENT DOCUMENTS

| | | | |
|---|---|---|---|
| 4,534,916 A | 8/1985 | Wichterle | 264/2.1 |
| 5,338,298 A * | 8/1994 | McIntyre | 604/103.07 |
| 5,356,591 A | 10/1994 | Pinchuk et al. | 264/573 |
| 5,358,486 A | 10/1994 | Saab | 604/96 |
| 5,755,690 A | 5/1998 | Saab | 604/96 |
| 6,004,289 A | 12/1999 | Saab | 604/96 |
| 6,176,698 B1 | 1/2001 | Grantz et al. | 425/522 |
| 6,221,043 B1 * | 4/2001 | Fischell et al. | 604/103.07 |
| 6,561,788 B1 * | 5/2003 | Gaudoin | 425/522 |
| 2001/0000350 A1 | 4/2001 | Durcan et al. | 623/1.11 |
| 2002/0125617 A1 | 9/2002 | Skinner et al. | 425/522 |
| 2002/0183780 A1 | 12/2002 | Wang | 606/194 |

FOREIGN PATENT DOCUMENTS

| | | |
|---|---|---|
| WO | WO 01/21245 | 3/2001 |
| WO | WO 02/41934 | 5/2002 |

OTHER PUBLICATIONS

PCT International Search Report mailed Jun. 1, 2004 for PCT/US03/41458 (filed Dec. 30, 2003).

* cited by examiner

Primary Examiner—Robert B. Davis

(57) ABSTRACT

A mold for forming medical balloons and the balloons formed therefrom are disclosed. The mold has a generally cylindrical inner molding surface for forming a working length of the balloon, and generally cylindrical outer molding surfaces at either end of the mold for forming shafts of the balloon. Joining these outer and inner molding surfaces are taper molding regions composed of two generally conical molding surfaces oriented at two different angles from a longitudinal axis of the mold. A balloon resulting from a manufacturing process using a mold according to the present invention reflects the geometry of the mold and has a unique concave taper profile and a well-defined working length.

19 Claims, 3 Drawing Sheets

MOLD FOR FORMING A MEDICAL BALLOON

BACKGROUND OF THE INVENTION

1. Field of the Invention

The present invention relates generally to an inflatable medical balloon, and more particularly, to a method and mold for fabricating medical balloons. The mold has a unique configuration with a dual angle taper region to provide both a more defined and distinct taper region, and optimally thin and flexible taper and shaft dimensions.

2. Background of the Invention

Inflatable medical balloons associated with balloon catheters are well known in the art, and are commonly used in, for example, percutaneous transluminal coronary angioplasty (PTCA) or delivery of a vascular stent or stent graft. During a PTCA procedure, a balloon catheter is used to dilate arteries obstructed by plaque in order to improve blood flow through the artery. Stents are used as prosthetic devices to support weakened or diseased vascular walls to avoid catastrophic rupture thereof. In either procedure, the balloon catheter is normally advanced through the patient's arterial system until the obstruction is reached. The balloon catheter must typically follow a narrow and tortuous path in order to reach the desired destination. Because of the difficulty of proceeding along such a pathway during a PTCA procedure or stent delivery, the balloon is advanced through the patient's arterial system in a deflated configuration, generally folded around the catheter to as low a profile as possible.

Medical balloons used for these procedures typically include a cylindrical main body/working length, shafts that attach the balloon to the catheter, and tapered transition regions that join the shafts to the main body. Ideally, the main body and the shafts would be connected perpendicularly, which would permit for a folded configuration with a very low profile. However, manufacturing limitations currently require the use of tapered transition regions, as the perpendicular transition region is extremely difficult to mold.

The process of fabricating such balloons using mold technologies is well known in the art. One example of a manufacturing process employing a mold is as follows. The process generally begins by placing an extruded cylindrical tubular parison made of a drawable polymer having a specified diameter and wall thickness into the cavity of a mold. The parison is then heated to a blowing temperature. While in this amorphous state, the parison is pressurized so that it will expand and the parison material will be forced against the inner molding surfaces of the mold cavity. Simultaneously with this expansion, the parison is also drawn longitudinally. The completed balloon is then removed from the mold.

Unfortunately, blowing medical balloons using mold technology is somewhat limited in its ability to form a clear and distinct taper region and working length transition that can be used to measure the working length of the balloon accurately. As a particular patient's arterial system and obstructions will reflect a specific geometry the physician performing the procedure will choose a balloon according to the dimensions of that balloon. Therefore, the physician must be able to know with precision the dimensions of the balloon.

Increasing the angle of the taper relative to the longitudinal axis of the mold can help make the working length more defined and distinct. However, the increased angle can make forming the shaft and taper sections of the balloon more difficult. The result can be undesirable artifacts in the balloon material, such as stretch marks and thickness anomalies, as well as suboptimal taper and shaft dimensions. For example, the dimensions of the taper and the shaft may be too thick, which would make the taper and the shaft less flexible and less capable of being folded to a low profile on the catheter.

BRIEF SUMMARY OF THE INVENTION

The aim of the present invention is to provide a mold suitable for manufacturing medical balloons that takes advantage of the best characteristics of a high taper angle and a low taper angle. The present invention is a mold that has a unique configuration with a dual angle taper region and includes balloons fabricated from such a mold. The mold has a high taper angle at a union of a balloon mold taper region and a balloon mold working length portion, which yields a more defined and distinct taper region in a molded balloon. At a union of the balloon mold taper region and a balloon mold shaft portion, the mold has a low taper angle to give a balloon molded therefrom optimally thin and flexible taper and shaft dimensions. A balloon made from a mold according to the present invention has an unique concave profile in a transition region thereof, the transition region being located between a shaft portion and a working length portion thereof.

BRIEF DESCRIPTION OF THE DRAWINGS

The foregoing and other features and advantages of the invention will be apparent from the following, more particular description of a preferred embodiment of the invention, as illustrated in the accompanying drawings.

DETAILED DESCRIPTION OF THE INVENTION

A preferred embodiment of the present invention is now described with reference to the figures, where like reference numbers indicate identical or functionally similar elements.

Figure 1:
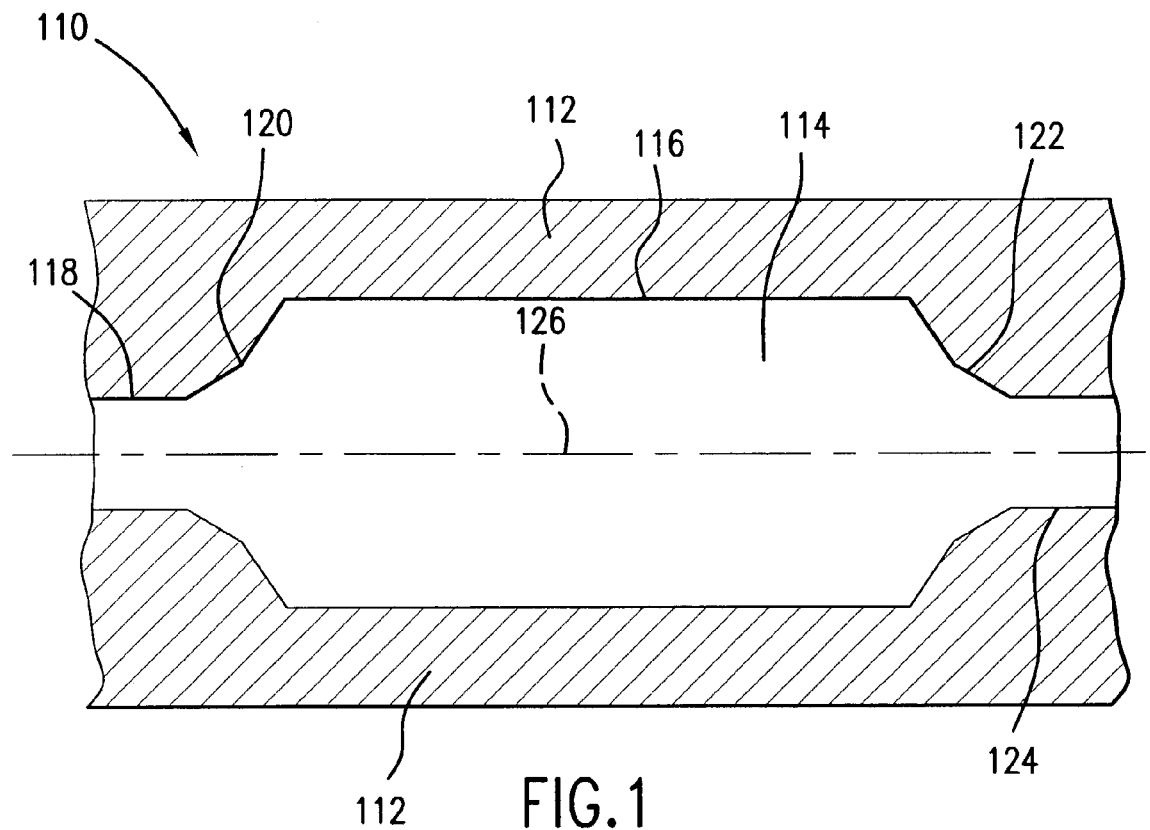
FIG. 1 is a sectional view of a mold in accordance with the present invention.

Referring now to FIG. 1, a mold 110 includes a mold body 112 defining a mold cavity 114 having a longitudinal axis 126 passes through the center of the mold cavity. In one embodiment of mold 110, the balloon mold is made from a metal material. Other materials are appropriate for mold 110, however, as the mold design does not limit the mold material. Also, the intended material choice for the balloon to be manufactured using mold 110 does not bear upon the choice of material for mold 110. Appropriate materials for mold 110 would include metals such as titanium, stainless steel, brass, and other copper alloys, and polymers, such as polycarbonate and polyolefins.

Mold cavity 114 has a generally cylindrical inner molding surface 116, a first generally cylindrical outer molding surface 118 located at the proximal end of mold cavity 114 and a second generally cylindrical outer molding surface 124 located at the distal end of mold cavity 114 and generally opposing first outer molding surface 118. The mold cavity has a first taper molding region 120 that joins first outer molding surface 118 and the proximal end of inner molding surface 116. At the distal end of inner molding surface 116 and generally opposing first taper molding region 120 is a second taper molding region 122 that joins second outer molding surface 124 and the distal end of inner molding surface 116.

Figure 2:
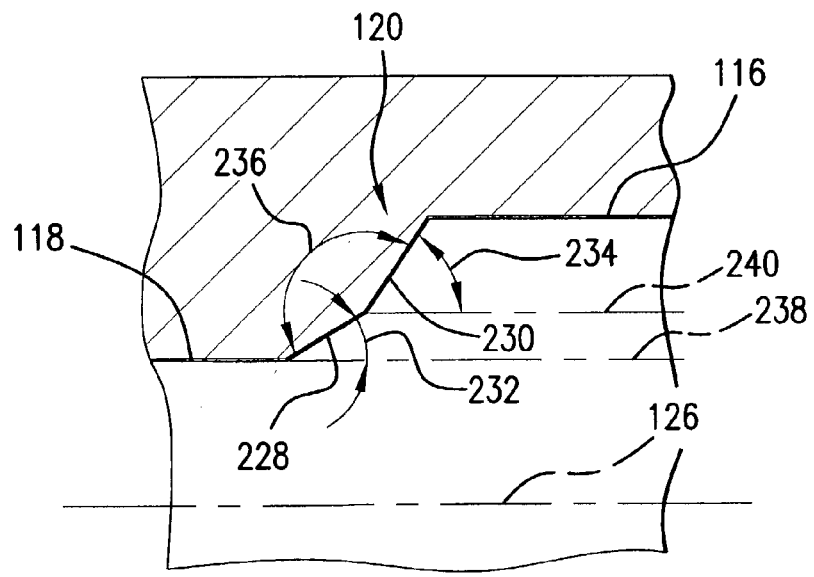
FIG. 2 is a sectional view of the upper half of the proximal taper region of the mold depicted in FIG. 1.

First and second taper molding regions 120, 122, respectively, are composed of two generally conical molding surfaces oriented at two different angles from longitudinal axis 126. As shown in FIG. 2, with reference to first taper molding region 120, the sum of a first angle 232 and a second angle 234 is preferably less than 180 degrees. FIG. 2 provides a detailed view of an upper half of the first taper molding region 120. Only first taper molding region 120 will be discussed in detail; however, it should be understood that second taper molding region 122 is simply a mirror image of first taper molding region 120.

Referring now to FIG. 2, a first generally conical molding surface 228 is oriented at first angle 232 from longitudinal axis 126. For the sake of clarity, a phantom line 238 that is parallel to the longitudinal axis 126 is provided to distinctly show the angle. First angle 232 is preferably a shallow, acute angle. The optimal range of angles for first angle 232 is between 15 and 20 degrees. In order to conform with standard production techniques, the preferred angle for first angle 232 is 20 degrees. The low taper angle makes the formation of the shaft and taper regions of the balloon much easier than a higher angle, resulting in fewer undesirable artifacts as well as optimization of the taper and shaft thickness.

A second generally conical molding surface 230 is oriented at second angle 234 from longitudinal axis 126. For the sake of clarity, a phantom line 240 that is parallel to longitudinal axis 126 is provided to distinctly show the angle. Second angle 234 is preferably a steep, acute angle. The optimal range of angles for second angle 234 is between 40 and 70 degrees. The preferred angle for second angle 234 is 50 degrees. The high taper angle helps to make the working length of the balloon much more defined and distinct.

The actual dimensions of the mold depend upon the desired dimensions of the resultant balloon. Preferably the length of a balloon in its taper region should be as short as possible so as to most closely approximate the ideal structure, wherein the balloon taper region is substantially disposed perpendicularly between the working length portion and the shaft portion of the balloon. In one embodiment, the overall length of first taper region 120 is approximately one-half the diameter of inner molding surface 116. Further, first conical molding surface 228 and second conical molding surface 230 are both approximately the same length, meeting at or near a center of first taper region 120.

Figure 3:
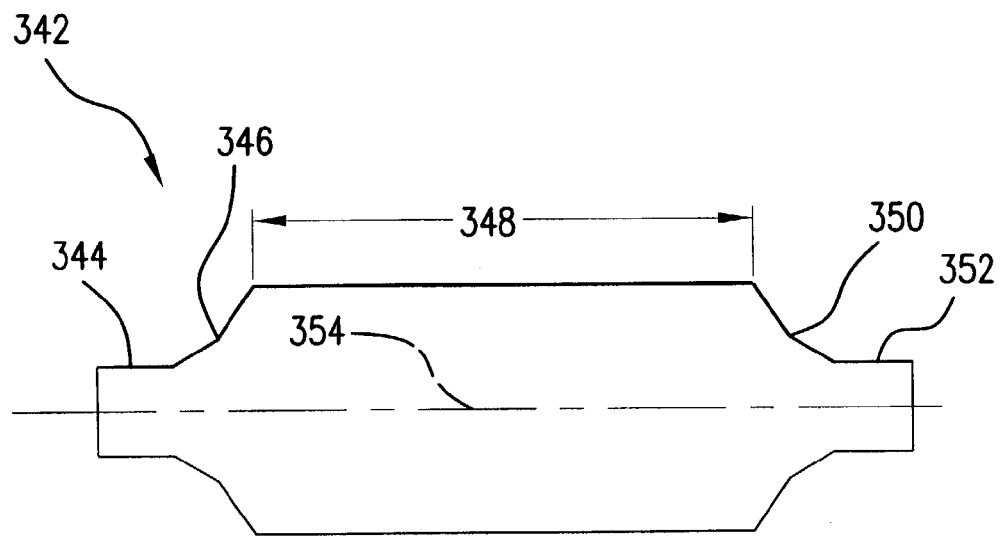
FIG. 3 is a sectional view of a balloon fabricated from the mold depicted in FIG. 1.

A balloon 342 is shown in FIG. 3. Balloon 342 is fabricated according to any of the existing balloon fabricating techniques that utilize molds. Such as the process described above. The material used for the balloon is preferably nylons but any standard medical balloon material could be used, such as polyethylene terephthalate, polyvinylchloride, PEBAX®, Pellethane, and the like. The choice of the material of the balloon is not dependent upon the material used for the mold.

Referring now to FIG. 3, balloon 342 formed using mold 110 retains the geometric characteristics of mold 110. Balloon 342 has a clear and distinct, generally cylindrical working length portion 348 and a longitudinal axis 354 passing through a center of balloon 342. At either end of balloon 342 are first and second generally cylindrical shaft portions 344, 352 respectively. These shaft portions are used to connect balloon 342 to a catheter shaft. Finally, joining working length portion 348 and shaft portions 344, 52 are first and second taper regions 346, 350 respectively.

Figure 4:
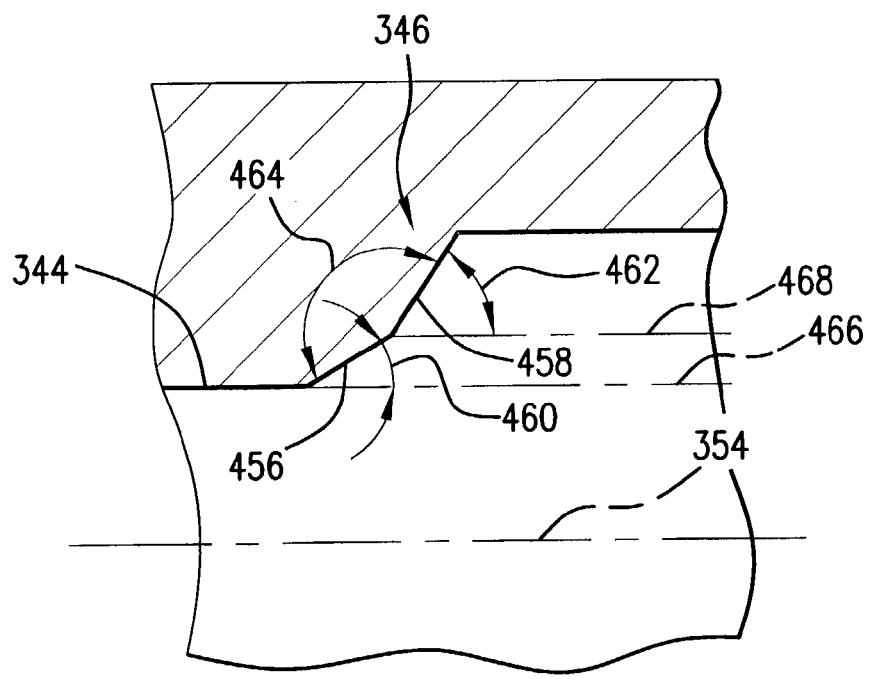
FIG. 4 is a sectional view of the upper half of the proximal taper region of the balloon depicted in FIG. 3.

Balloon taper regions 346, 350 have a generally concave profile. Referring now to FIG. 4, the concave profile of an upper half of first taper region 346 is shown in greater detail. First taper region 346 is made of a first generally conical segment 456 at a first angle 460 from balloon longitudinal axis 354 and a second generally conical segment 458 oriented at a second angle 462 from the balloon longitudinal axis 354. In order to maintain the concave profile of first taper region 346, a balloon taper region angle 464 must be less than 180 degrees.

First angle 460 formed by a juncture of balloon cylindrical shaft portion 344 and balloon first taper region 346 is shown using a phantom line 466 that runs parallel to balloon longitudinal axis 354. First angle 460 is preferably a shallow acute angle, as such an angle minimizes undesirable artifacts in cylindrical shaft portion 344 and taper region 346. In one embodiment of the present invention, an optimal range of angles for first angle 460 is from 15 to 20 degrees. A balloon with this type of taper region will have shaft and taper region dimension particularly suited to obtaining a low profile and maintaining optimal flexibility once collapsed and folded around a catheter shaft.

Second angle 462 formed by a juncture of first taper region 346 and an end of balloon working length portion 348 is shown using a phantom line 468 that runs parallel to balloon longitudinal axis 354. Second angle 462 is preferably a steep acute angle as such an angle assists in the formation of a clear and distinct working length during manufacturing. In one embodiment of the present invention, an optimal range of angles for second angle 462 is between 40 and 70 degrees. A physician performing a PTCA or stent delivery procedure will choose a particular balloon for the procedure according to the length of the diseased portion of the vessel. The physician will then match the working length dimension of the balloon to the length of the diseased portion of the vessel. Therefore, the ability to know with precision the working length dimension of the balloon is critical to a successful procedure, as it limits the unintentional treatment of the undiseased portion of the vessel.

Medical balloons come in a variety of dimensions, in order to enable a physician to customize the procedure to a particular blockage within a patient. Therefore, the dimensions of balloons produced according to the present invention, specifically a working length and a fully expanded diameter, will vary greatly. However, an overall length of first taper region 346 is preferably one half a diameter of balloon working length portion 348. In a preferred embodiment, first and second taper region conical segments 456, 458 are approximately equal in length and meet at or near a center of first taper region 346.

Figure 5:
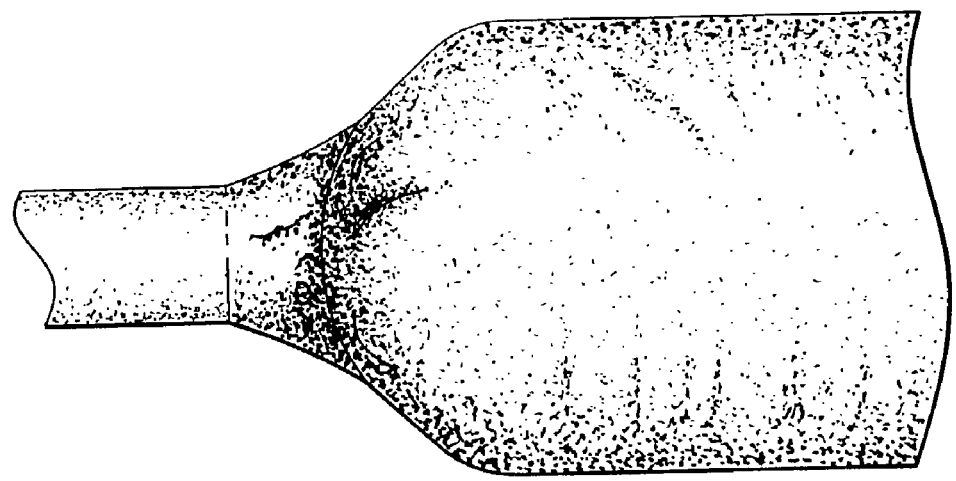
FIG. 5 is a photograph of one end of a balloon fabricated from the mold depicted in FIG. 1, where the balloon is at low inflation pressure.
Figure 6:
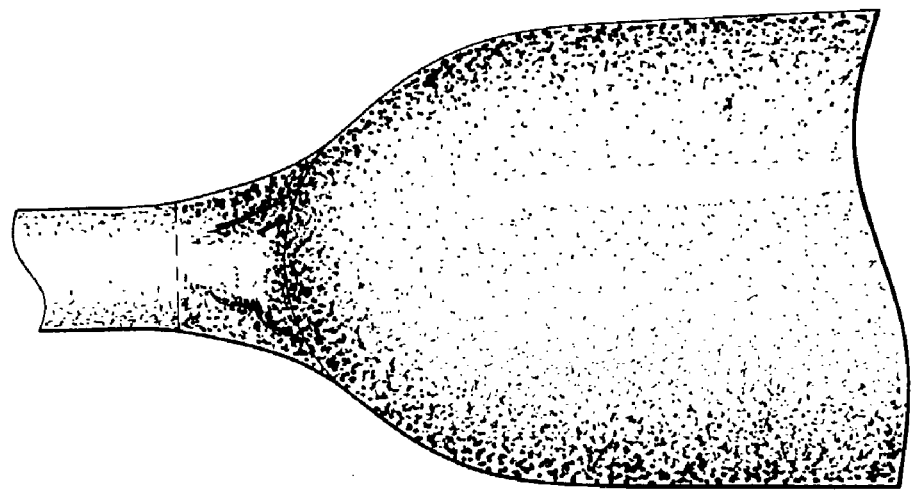
FIG. 6 is a photograph of the same end of the same balloon depicted in FIG. 5, where the balloon is at a higher inflation pressure.

At low inflation pressures, approximately 30 psi to 60 psi, a unique concave profile of a balloon made in a mold according to the present invention is clearly visible. This geometry can be seen in FIG. 5, which shows a balloon of the present invention at low inflation pressure. However, at higher inflation pressures, the concave profile of the balloon is lost, and the balloon takes on a hemispherical shape common to many medical balloons at higher inflation pressures. This hemispherical shape can be seen clearly in FIG. 6, which shows a balloon at high inflation pressure, which is greater than 120 psi.

While specific embodiments of the present invention have been described in detail, those skilled in the art will appreciate that various modifications and alternatives to those details could be developed in light of the overall teachings of the disclosure. Accordingly, the particular arrangement disclosed is meant to be illustrative only and does not limit the scope or the spirit of the invention, which is to be given the full breadth of the claims and any equivalents thereof.

What is claimed is:

1. A mold for forming an inflatable medical balloon having a mold body defining at least one internal mold cavity, said internal mold cavity comprising:
    a proximal end and a distal end along a longitudinal axis passing through said internal mold cavity;
    a generally cylindrical inner molding surface having a diameter;
    first and second generally cylindrical outer molding surfaces located respectively at said proximal end and said distal end of said internal mold cavity; and
    first and second taper regions located, respectively, proximally and distally of said inner molding surface, each taper region having a length approximately one-half the diameter of the cylindrical inner molding surface
    a first generally conical taper molding surface oriented at a first angle connecting the outer molding surface and a second generally conical taper molding surface, and
    the second taper molding surface oriented at a second angle connecting the first taper molding surface and the inner molding surface.

2. The mold of claim 1, wherein the generally conical molding surfaces are frusta.

3. The mold of claim 1, wherein a diameter of the generally cylindrical inner molding surface varies along the longitudinal axis of the mold cavity.

4. The mold of claim 1, wherein the mold is made of polymer.

5. The mold of claim 1, wherein the mold is made of metal.

6. The mold of claim 1, wherein the sum of the first and second angles is less than 180 degrees.

7. The mold of claim 6, wherein the first angle and the second angle of the generally conical molding surfaces are both acute angles.

8. The mold of claim 5, wherein the first angle is a shallow acute angle.

9. The mold of claim 6, wherein the first angle is between 15 and 20 degrees.

10. The mold of claim 6, wherein the second angle is a steep acute angle.

11. The mold of claim 6, wherein the second angle is between 40 and 70 degrees.

12. An inflatable medical balloon with a shape discernable at low inflation pressures comprising:
    a proximal and distal end along a longitudinal axis passing through the balloon;
    a generally cylindrical working length having a diameter;
    first and second generally cylindrical shaft portions at the proximal and distal ends of the balloon, respectively; and
    first and second generally concave, conical taper regions connecting the working length to the first and second shaft portions, respectively, the first and second taper regions having a length approximately one half the cylindrical working length diameter.

13. The balloon of claim 12, wherein each of the taper regions includes a first generally conical region oriented at a first angle from the longitudinal axis of the balloon and a second generally conical region oriented at a second angle from the longitudinal axis of the balloon.

14. The balloon of claim 13, wherein the sum of the first and second angles is less than 180 degrees.

15. The balloon of claim 13, wherein the first and second angles are both acute angles.

16. The balloon of claim 13, wherein the first angle is a shallow acute angle.

17. The balloon of claim 13, wherein the first angle is between 15 and 20 degrees.

18. The balloon of claim 13, wherein the second angle is a steep acute angle.

19. The balloon of claim 13, wherein the second angle is between 40 and 70 degrees.

* * * * *